United States Patent
Peuker et al.

(10) Patent No.: US 9,827,070 B2
(45) Date of Patent: Nov. 28, 2017

(54) APPLICATION TIP AND SYSTEM FOR DISPENSING A DENTAL MATERIAL

(71) Applicant: 3M INNOVATIVE PROPERTIES COMPANY, St. Paul, MN (US)

(72) Inventors: Marc Peuker, Schöndörf (DE); Andreas J. Boehm, Reichling (DE)

(73) Assignee: 3M Innovative Properties Company, St. Paul, MN (US)

( * ) Notice: Subject to any disclaimer, the term of this patent is extended or adjusted under 35 U.S.C. 154(b) by 199 days.

(21) Appl. No.: 14/401,696

(22) PCT Filed: May 6, 2013

(86) PCT No.: PCT/US2013/039608
§ 371 (c)(1),
(2) Date: Nov. 17, 2014

(87) PCT Pub. No.: WO2013/176870
PCT Pub. Date: Nov. 28, 2013

(65) Prior Publication Data
US 2015/0118646 A1   Apr. 30, 2015

(30) Foreign Application Priority Data
May 25, 2012 (EP) .................................... 12169474

(51) Int. Cl.
*A61C 5/04* (2006.01)
*A61C 17/00* (2006.01)
(Continued)

(52) U.S. Cl.
CPC ................ *A61C 5/062* (2013.01); *A61C 5/62* (2017.02); *A61C 5/66* (2017.02); *A61C 9/0033* (2013.01)

(58) Field of Classification Search
CPC ......... A61C 5/062; A61C 9/0033; A61C 5/066; A61C 1/08; A61C 1/081; A61C 5/04;
(Continued)

(56) References Cited

U.S. PATENT DOCUMENTS 5,083,921 A    1/1992 Dragan
5,490,779 A  * 2/1996 Malmin ................... A61C 5/40
                                                                433/224

(Continued)

FOREIGN PATENT DOCUMENTS

EP    1 226 790    1/2002
EP    1269968     1/2003
(Continued)

OTHER PUBLICATIONS

"GC FujiCEM Paste A", Material Safety Data Sheet (Product safety data sheet of GC FujiCEM Paste A), GC FujiCEM Automix, Jul. 2007, 6pgs.

(Continued)

*Primary Examiner* — Joshua Lee
*Assistant Examiner* — Garrett Atkinson (57) ABSTRACT

An application tip for dispensing a dental material has a tubular dispensing end made of a plastic material. The dispensing end being formed of a circumferential wall having a thickness $T_1$ and which forms a dispensing opening of a diameter $D_{i1}$ and having a diameter-to-thickness-ratio $D_{i1}:T_1$ at the opening which is 13 or greater. The wall thickness increases in a direction away from the opening. The application tip preferably facilitates appropriately depositing the dental material.

14 Claims, 5 Drawing Sheets

(51) Int. Cl.
*A61C 5/06* (2006.01)
*A61C 9/00* (2006.01)
*A61C 5/62* (2017.01)
*A61C 5/66* (2017.01)

(58) Field of Classification Search
CPC .............. A61C 7/00; A61C 17/02; A61C 19/06–19/063; A61V 1/087
USPC .............. 433/80, 81, 88–90, 215, 217.1
See application file for complete search history.

(56) References Cited

U.S. PATENT DOCUMENTS

| | | | |
|---|---|---|---|
| 5,722,830 A | | 3/1998 | Brandhorst |
| 6,398,761 B1 * | | 6/2002 | Bills .................. A61C 9/0026 222/145.5 |
| 7,320,596 B2 | | 1/2008 | Metzbower |
| 8,882,502 B2 | | 11/2014 | Pauser |
| D754,539 S * | | 4/2016 | Eckstein .................. D9/447 |
| 2003/0096212 A1 | | 5/2003 | Cheetham |
| 2003/0186191 A1 * | | 10/2003 | Lawter .................. A61C 5/62 433/90 |
| 2007/0262178 A1 * | | 11/2007 | Fischer .................. A61C 5/62 239/602 |
| 2009/0042162 A1 * | | 2/2009 | Pond .................. A61C 17/0202 433/80 |
| 2010/0081111 A1 * | | 4/2010 | Better .................. A61C 8/0018 433/174 |
| 2010/0239998 A1 * | | 9/2010 | Snyder .................. A61C 17/02 433/29 |
| 2011/0151403 A1 * | | 6/2011 | Pauser .................. A61C 5/62 433/82 |
| 2011/0223556 A1 * | | 9/2011 | Abel .................. A61C 9/00 433/90 |
| 2012/0045730 A1 * | | 2/2012 | Sayder .................. A61C 17/02 433/29 |
| 2012/0045732 A1 | | 2/2012 | Chen |
| 2012/0064482 A1 * | | 3/2012 | Boehm .................. A61C 5/62 433/90 |
| 2012/0077142 A1 | | 3/2012 | Maurer |
| 2012/0134738 A1 * | | 5/2012 | Habibi-Naini .......... A46B 11/00 401/288 |
| 2012/0258420 A1 * | | 10/2012 | Boehm .................. A61C 9/0026 433/89 |
| 2012/0329006 A1 * | | 12/2012 | Pierson .................. A61C 9/0026 433/90 |

FOREIGN PATENT DOCUMENTS

| | | | |
|---|---|---|---|
| EP | 1790323 | 5/2007 | |
| EP | 2255748 | 12/2010 | |
| EP | 2255748 A1 * | 12/2010 | ............. A61K 6/027 |
| FR | 2826862 | 1/2003 | |
| JP | 02-037608 | 3/1990 | |
| WO | WO 97-00065 | 1/1997 | |
| WO | WO 03-086328 | 10/2003 | |
| WO | WO 2005-055854 | 6/2005 | |

OTHER PUBLICATIONS

"GC FujiCEM Paste B", Material Safety Data Sheet (Product safety data sheet of GC FujiCEM Paste B), GC FujiCEM Automix, Jul. 2007, 5pgs.
"GC FujiCEM Resin-Modified Glass Ionomer cement in Paste-Pak Dispensing System", Product brochure of GC FujiCEM Automix, GC America Inc., 2008, 2pgs.
"Radiopaqe reinforced glass ionomer luting cement", Instruction manual of GC FujiCEM/GC FujiCEM Automix, GC Corporation, Apr. 2008, 4pgs.
Irie, "Marginal and flexural integrity of three classes of luting cement, with early finishing and water storage", Dental Materials, 2004, vol. 20, pp. 3-11.
1507 Extended EP Search Report for EP12169474.9, PCT/US2013/039608, dated Oct. 17, 2012, 6 pgs.
International Search Report for PCT International Application No. PCT/US2013/039608, dated Jul. 9, 2013, 4pgs.

* cited by examiner

APPLICATION TIP AND SYSTEM FOR DISPENSING A DENTAL MATERIAL

FIELD OF THE INVENTION

The invention relates to an application tip for dispensing a dental material, and in particular to an application tip which has a tubular dispensing end which is configured such that it is preferably resiliently deformable in cross-section. Further the invention relates to a system for dispensing dental material.

BACKGROUND ART

Dental materials are often stored in packages from which they can be directly dispensed to a desired location. Such packages typically have a dispensing nozzle which is sized according to the material to be dispensed and to requirements related to the application, for example an intended dental treatment. For example a nozzle for dispensing a high viscosity material or for dispensing the material at a high flow rate may have a relatively wide conduit to avoid too high forces required to dispense material from the nozzle. On the other hand some dental treatments require a relative thin nozzle to precisely deposit the material at a desired location, for example on a dental restoration or in a patient's mouth.

There are packages which can be used in combination with exchangeable application tips of different shapes and configurations to adapt the package for different applications. For example a thin tip may be used to precisely deposit a material, whereas a wider tip may be used to dispense the material at a higher flow rate.

Further FR 2 826 862 discloses an adaptable end on a syringe for dental material which has a nozzle whose diameter at the front most end is lower than 0.90 mm, preferably about 0.68 to 0.70 mm, in order to allow the nozzle to be inserted in a patient's sulcus. The nozzle is adapted such that, for example once inserted in the sulcus, widens upon material being urged through the nozzle.

Although existing packages for dental material provide certain advantages there is still a need for an application tip which can be used in different applications, which is easy to manufacture and relatively inexpensive.

SUMMARY OF THE INVENTION

In one aspect the invention relates to an application tip for dispensing a dental material. The application tip has a tubular dispensing end made of a plastic material. Further the dispensing end is formed of a circumferential wall having a thickness $T_1$ and which forms a dispensing opening of a diameter $D_{i1}$. The dispensing end has a diameter-to-thickness-ratio $D_{i1}:T_1$ at the opening which is at least 13 or greater. Further the wall thickness increases in a direction away from the opening.

The invention is advantageous in that the application tip preferably is self adapting to narrow spaces. In particular the invention may be advantageous in that the application tip adjacent the opening is preferably adapted to conform into an corner, as for example present in a tooth cavity prepared by a dentist to receive a dental filling material. Further the invention preferably facilitates application of the dental material and may particularly minimize any need to use different application tips for a dental treatment. Further the application tip and system of the invention are preferably relative inexpensive to manufacture.

In one embodiment the dispensing end has a diameter-to-thickness-ratio $D_{i1}:T_1$ at the opening which is within a range of 13 to 30, in particular within a range of 13 to 25.

In one embodiment the diameter $D_{i1}$ is within a range of 1 mm to 2.5 mm, particularly within a range of 1.2 mm to 2.5 mm, or a range of 1.5 mm to 2.5 mm. Further the thickness $T_1$ is preferably within a range of 0.05 mm and 0.19 mm. The dispensing end may have an outer conical shape and an inner conical shape. The inner cone is defined between a first smaller diameter $D_{i1}$ and a second greater diameter $D_{i2}$, wherein the first diameter $D_{i1}$ of the inner cone corresponds to the diameter $D_{i1}$ of the opening. Further the outer cone is defined between a first smaller diameter $D_{o1}$ and a second greater diameter $D_{o2}$, wherein the first diameter $D_{o1}$ of the outer cone is determined by the formula $D_{o1}=D_{i1}+2*T_1$. Further the inner cone and the outer cone have a length L between their smaller and greater diameters. The length L may correspond to a length of the dispensing end. In preferred embodiments the length L is within a range of about 4 mm and about 25 mm, preferably within a range of about 8 mm and about 15 mm.

Based on the length L the ratio $D_{i1}:D_{i2}$ of the first diameter and the second diameter of the inner cone relative to each other is within a range of about 0.4 and about 1, preferably about 0.7. Further also based on the length L the ratio $D_{o1}:D_{o2}$ of the first diameter and the second diameter of the outer cone relative to each other is within a range of about 0.3 and about 0.9, preferably about 0.6. In addition at the length L (or at the inner and outer second diameter $D_{i2}$, $D_{o2}$) the dispensing end has a second wall thickness $T_2$ which is greater than the wall thickness $T_1$ at the opening. Preferably the second wall thickness is within a range of about 0.075 mm and about 0.5 mm, preferably about 0.3 mm.

In one embodiment the ratio $D_{i1}:D_{i2}$ of the first diameter and the second diameter of the inner cone relative to each other is greater than 1, for example about 1.1. Notwithstanding the teaching above the skilled parson will recognize that in this case of the two diameters the diameter $D_{i1}$ is the greater diameter and the diameter $D_{i2}$ the smaller diameter.

Further also based on the length L the ratio $D_{o1}:D_{o2}$ of the first diameter and the second diameter of the outer cone relative to each other is within a range of about 0.3 and about 0.9, preferably about 0.6. In addition at the length L (or at the inner and outer second diameter $D_{i2}$, $D_{o2}$) the dispensing end has a second wall thickness $T_2$ which is greater than the wall thickness $T_1$ at the opening. Preferably the second wall thickness is within a range of about 0.075 mm and about 0.5 mm, preferably about 0.3 mm.

In one embodiment the plastic material is a first plastic material selected among polyethylene (PE), polypropylene (PP), polyoxymethylene (POM), polybutadiene terephthalate (PBT), acrylonitrile-butadiene-styrene terpolymer (ABS), and polyamide (PA). Further the plastic material may be a second plastic material selected from among a thermoplastic elastomer, silicone or rubber material.

In one embodiment the wall that forms the dispensing end comprises a first wall portion made of one of the first and second plastic material and a second wall portion made of the other one of the first and second plastic material. Accordingly one part of the dispensing end may be made of the first plastic material, and the remaining part of the dispensing end may be made of the second plastic material. The first wall portion and the second wall portion are arranged in a circumferentially alternating manner. For example one circumferential segment of the dispensing end may be made of the first plastic material and may extend entirely along the length of the dispensing end and another circumferential segment may be made of the second plastic material. Thus the first and second plastic material may extend in stripes along the length of the dispensing end.

In another embodiment the wall that forms the dispensing end comprises a first wall portion formed of the first plastic material and a second wall portion formed of the second plastic material. In this embodiment the second wall portion is preferably arranged adjacent the opening and the first wall portion is arranged further away from the opening. This may provide the dispensing end with a relatively high resistance against buckling and further with an elastic deformability at relatively low forces of the front most end of the dispensing end.

In a further embodiment the application tip has a predetermined breaking linkage in the transition between the first and second wall portions of the wall that forms the dispensing end. Thus a user may remove the second wall portion and use the dispensing end with only the remaining first wall portion. This first wall portion may form a second opening which is greater than the opening formed within the second wall portion. Accordingly in a dental treatment for example a dentist may use the dispensing end of the invention to precisely deposit a dental material in an corner of a tooth cavity, remove the second wall portion and use the dispensing end with only the first wall portion for bulk filling of the cavity. Thereby the greater diameter of the second opening may facilitate extrusion of the dental material at higher flow rates.

In one embodiment the first and second wall portion are linked by a positive fit or friction fit. Thus a user, for example dentist, may separate the first and second wall portions easily from each other.

In another embodiment the wall that forms the dispensing end has at least one slit extending from the opening in a direction away from the opening. Accordingly the wall may be in an arrangement in which wall portions overlap. Thus a deformation is enabled by means of a elastic deformation in combination with a variation of the overlap.

In a further aspect the invention relates to a system for dispensing a dental material. The system comprises the application tip according to the invention. Further the system comprises a cartridge with a chamber for holding the dental material and a piston which is movably arranged within the chamber for extruding the dental material.

In one embodiment the application tip and the cartridge are formed in one piece. For example the application tip and the cartridge may be entirely molded from a unitary plastic material within a single molding step and thus may be monolithically formed.

In another embodiment the application tip and the cartridge are formed in at least two separate pieces and being adapted for connecting with each other. The cartridge may comprise an outlet nozzle for the dental material, and the application tip and the outlet nozzle may be adapted for retaining with each other. The application tip in this embodiment may have a coupling for retaining with the outlet nozzle of the cartridge. Such a coupling may be selected from among a thread, a bayonet lock, a self-retaining cone connection and a Luer-Lock™, for example. The outlet nozzle of the cartridge may further have a corresponding coupling for mating with the coupling of the application tip.

In a further embodiment the cartridge may have a retainer for retaining the cartridge in a dispensing gun for dispensing the dental material from the cartridge. Such a retainer may for example be formed by a circumferential rim around an outer surface of the cartridge.

In one embodiment the system further comprises a dispensing gun for removably receiving the cartridge. Such a dispensing gun may comprise a plunger for urging the piston within the cartridge forward for dispensing the dental material. A dispensing gun as it may be used with the present invention is for example available under the designation 3M™ ESPE™ Restorative Dispenser for Capsules from 3M Deutschland GmbH.

In a further embodiment the system comprises a dental restorative material selected from among a composite, a bis-acrylic composite, and a glass ionomer. The system may further comprise a gingival retraction material or prophylaxis material.

In a further aspect the invention relates to a method of dispensing a dental material, comprising the steps of:
 providing an application tip having a tubular dispensing end made of a plastic material, the dispensing end being formed of a circumferential wall having a thickness $T_1$ and which forms a dispensing opening of a diameter $D_{i1}$, the dispensing end having a diameter-to-thickness-ratio $D_{i2}:T_1$ at the opening which is at least 13 or greater, preferably within a range of 13 to 25, and wherein the wall thickness increases in a direction away from the opening;
 forcing the dispensing end into a curve or bend formed by a surface and thereby causing the dispensing end to laterally deform.

The deformation is preferably temporary, preferably an elastic deformation. The deformation is preferably such that the dispensing end laterally flattens. Preferably the deformation is such that the dispensing end dimensionally reduces in one direction while it dimensionally enlarges in another dimension. For example the dispensing end may deform from a general circular lateral cross-section toward an elliptic lateral cross-section. In this regard the term lateral refers to a dimension perpendicular to a longitudinal axis of the application tip.

The method may further comprise the step of dispensing the dental material through the deformed application tip. Further the method may comprise the step of moving the application tip along a surface during maintaining dispensing and keeping the dispensing end deformed.

DETAILED DESCRIPTION OF THE INVENTION

Figure 1:
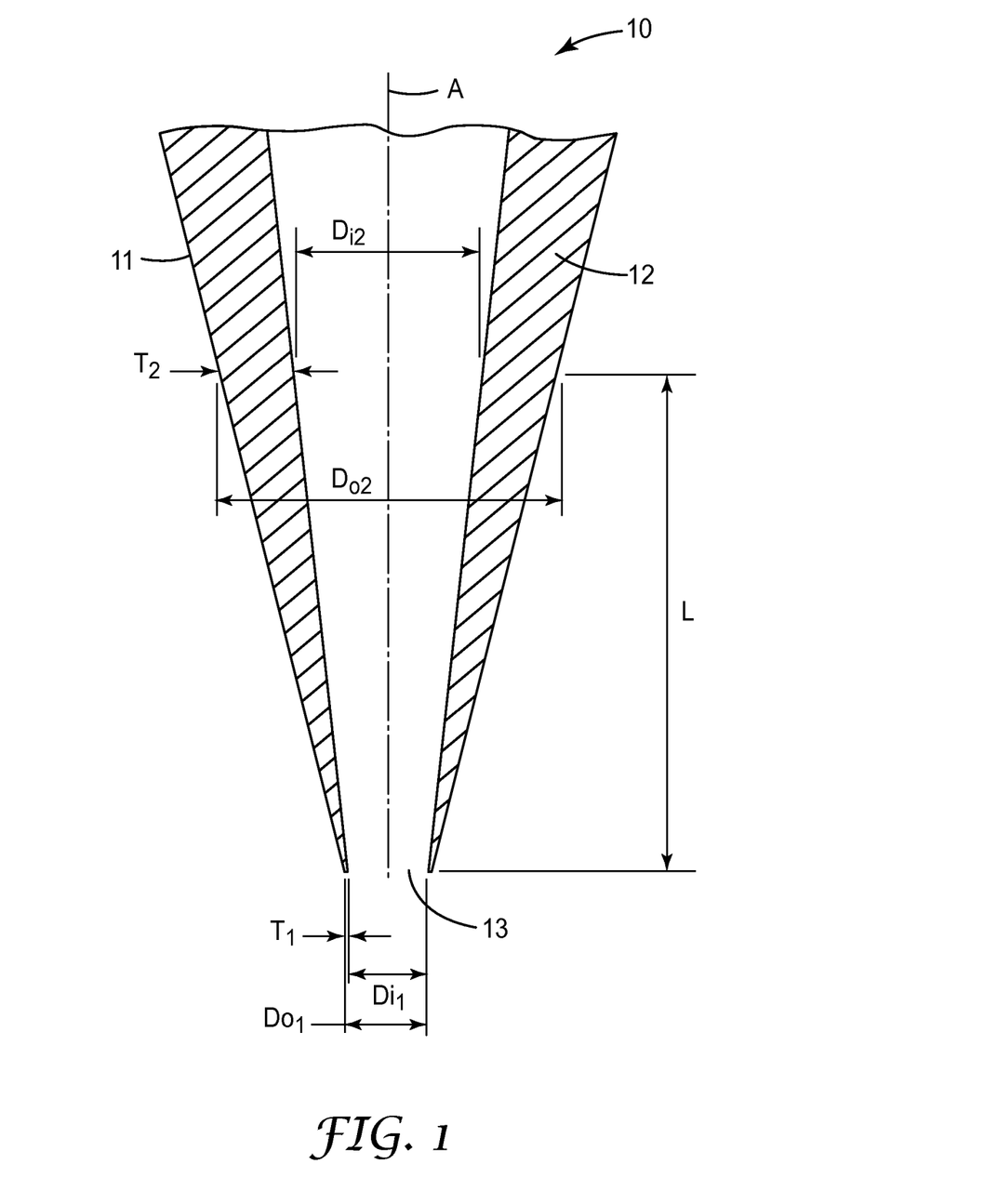
FIG. 1 is a cross-sectional view of an application tip according to an embodiment of the invention.
Figure 2:
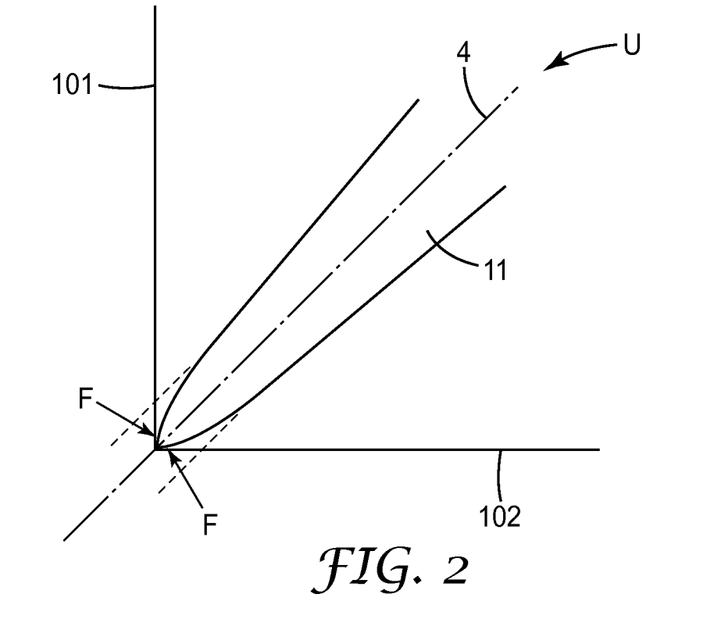
FIG. 2 is a side view of the application tip shown in FIG. 1.

FIG. 1 shows a portion of an application tip 10 for dispensing a dental material. In particular the Figure shows a dispensing end 11 that extends along a longitudinal axis A. Although the longitudinal axis A in the example shown is straight, the skilled person will recognize that in another example the longitudinal axis may be curved without departing from the invention. The dispensing end 11 is formed of a circumferential wall 12 and forms a dispensing opening 13. The dispensing end 11 has a generally circular ring shaped cross-section. In the example the dispensing end has an outer conical surface and an inner conical surface. The inner conical surface forms at least part of a conduit through the application tip 10 and forms the opening 13 at one end. At the dispensing opening 13 the wall 12 tapers off to form a resilient front most end. In particular at the dispensing opening 13 the wall 12 has a thickness $T_1$ and the opening has a diameter $D_{i1}$. The diameter $D_{i1}$ of the opening 13 and the wall thickness $T_1$ form a predetermined diameter-to-thickness-ratio $D_{i1}:T_1$ at the opening 13. The diameter-to-thickness-ratio is determined to permit a deformation of the dispensing end in response of a one-dimensional force in a dimension lateral to the longitudinal axis as illustrated in FIG. 2. In the example the dispensing end 11 has a diameter-to-thickness-ratio ($D_{i1}:T_1$) within a range of 13 to 25. Further the wall thickness increases in a direction away from the opening 13. For example at a distance L from the opening 13 the wall thickness $T_2$ is greater that the wall thickness $T_1$ at the opening. This preferably provides the dispensing end 11 with a sufficient buckling resistance upon exposing the dispensing end 11 with a pushing force in a direction of the longitudinal axis A.

FIG. 2 illustrates for the purpose of explaining the function and properties of the application tip the dispensing end 11 in a situation urged into an corner formed by two perpendicularly arranged surfaces 101, 102. A force U represents the force at which the dispensing end 11 is pushed toward the corner. Due to the resilient properties the dispensing end 11 generally conforms to the corner. In particular the dispensing end 11 flattens laterally to the longitudinal axis A in one dimension in response of the lateral forces F. Lateral forces F originate from the pushing force U in interaction with the surfaces 101, 102. Because of the flattening the dispensing end 11 is enabled to enter deeper into the corner than it would be enabled to without the flattening.

Figure 3:
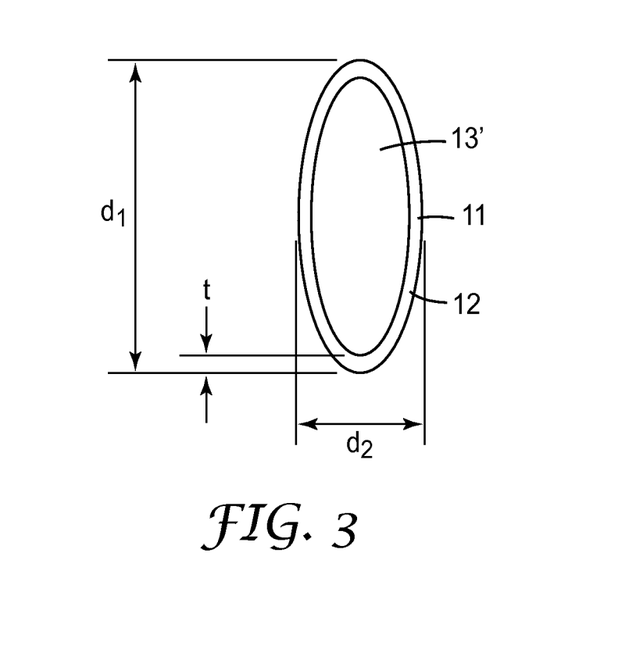
FIG. 3 is a front view of the application tip shown in FIG. 1.

FIG. 3 schematically illustrates the front most end of the dispensing tip 11 in the situation shown in FIG. 2, but from a perspective in a direction of the longitudinal axis A (see FIG. 2). The dispensing end 11 in the situation shown has a non-circular, in particular generally oval, ring shaped cross-section. This is indicated by the measures d1 and d2. The measures d1 and d2 are defined in the plane of the opening and in two perpendicularly arranged dimensions. The measure d2 is smaller than the measure d1. Further the measure d2 is smaller than the original diameter of the opening, and the measure d1 is greater than the original diameter of the opening. Accordingly relative to the circular cross-section illustrated in FIG. 1 the non-circular cross-section further results in an opening 13' which is reduced in its open area. Therefore the dispensing end 11 further causes the flow resistance for the dental material to increase with increasing deformation (flattening) of the tip 11. It has been found that thus the control of the flow rate of the dental material into an corner, as it may for example be present at a tooth to be restored, can be facilitated. Further due to the flattening and conforming properties of the dispensing end 11 the dental material may be precisely placeable in the corner.

In one example the diameter of the opening is about 1 mm and the wall thickness at the opening is about 0.05 mm, whereas in another example the opening is about 2.5 mm and the wall thickness at the opening is in a range of about 0.1 mm to 0.19 mm. It has been found that a dispensing end having diameter-to-thickness-ratio within the range of 13 to 25 at the opening provides a resilience of the dispensing end which permits it to conform into an corner in which it is manually pushed.

Figure 4:
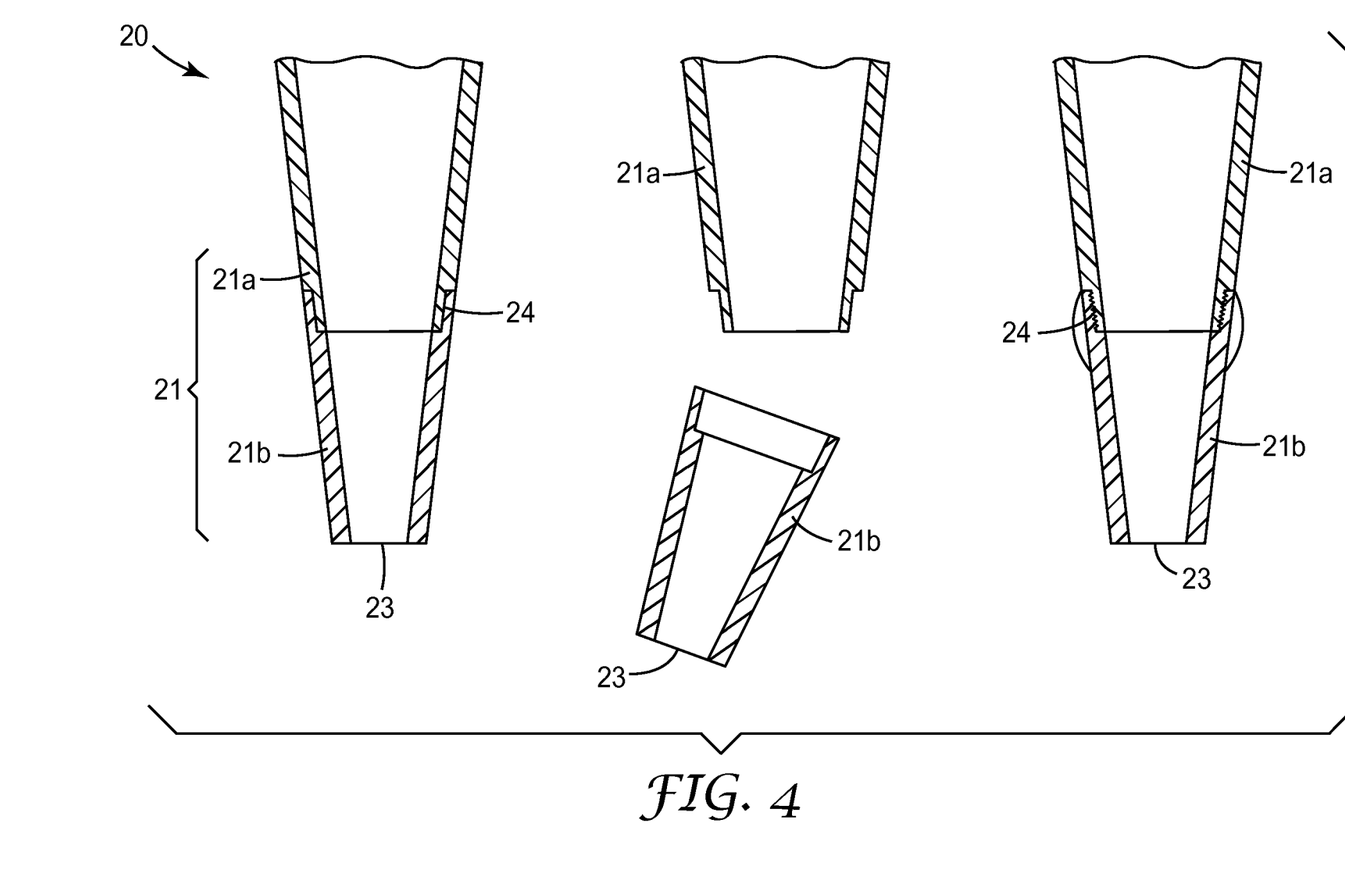
FIG. 4 are cross-sectional views of an application tip according to a further embodiment of the invention.

FIG. 4 shows an application tip 20 having dispensing end 21 which comprises a first wall portion 21a and a second wall portion 21b. The first wall portion 21a is made of a first plastic material and the second wall portion 21b is made of a different second plastic material. The first plastic material is preferably less resilient than the second plastic material. Further the first plastic material may be selected from among polyethylene (PE), polypropylene (PP), polyoxymethylene (POM), polybutadiene terephthalate (PBT), acrylonitrile-butadiene-styrene terpolymer (ABS), and polyamide (PA). The second plastic plastic material may be selected from among a thermoplastic elastomer, silicone or rubber material. As shown the second wall portion 21b forms an opening 23 and is preferably formed of the second plastic material, whereas the first wall portion 21a further away from the opening 23 is formed from the first plastic material.

In the example the application tip 20 has a predetermined breaking linkage 24 in the transition between the first and second wall portions 21a, 21b. In particular the first wall portion and the second wall portion are linked by a positive fit or friction fit. Thus the second wall portion 21b may be removable from the first wall portion. Thus the opening of the application tip may be increased, for example manually by a user.

Figure 5:
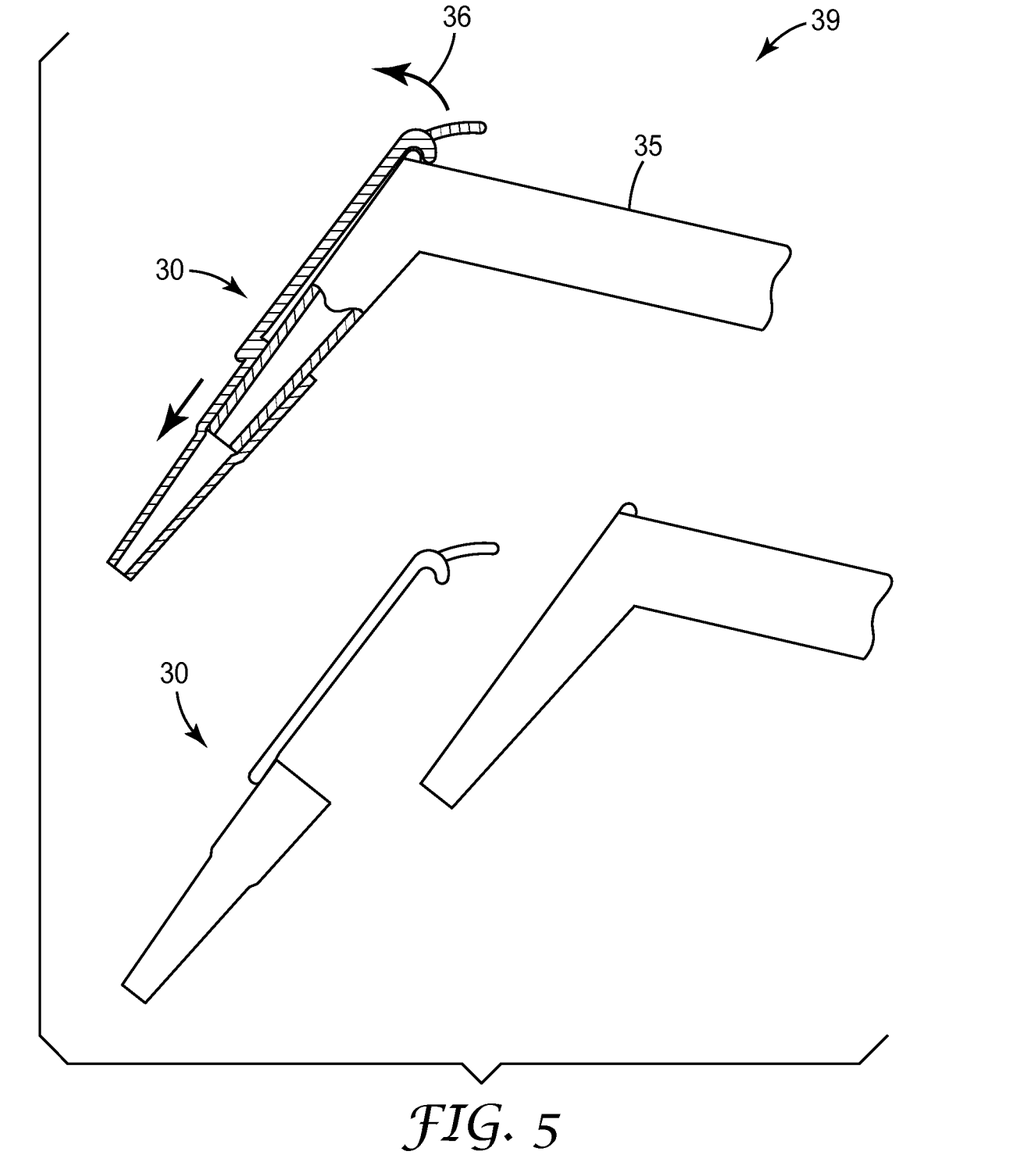
FIG. 5 are side views of a system for dispensing a dental material according to an embodiment of the invention.

FIG. 5 shows a system 39 for dispensing a dental material. The system 39 has an application tip 30 which is adapted for removably coupling with a dispensing nozzle of a cartridge 35. The application tip 30 may be generally configured as described in the examples shown in FIGS. 1 to 4. Further the application tip 30 in the example has a retention mechanism 36 for retaining with the cartridge 35. The skilled person will recognize further retention mechanisms, like for example a thread or Luer-Lock™ connection.

Figure 6:
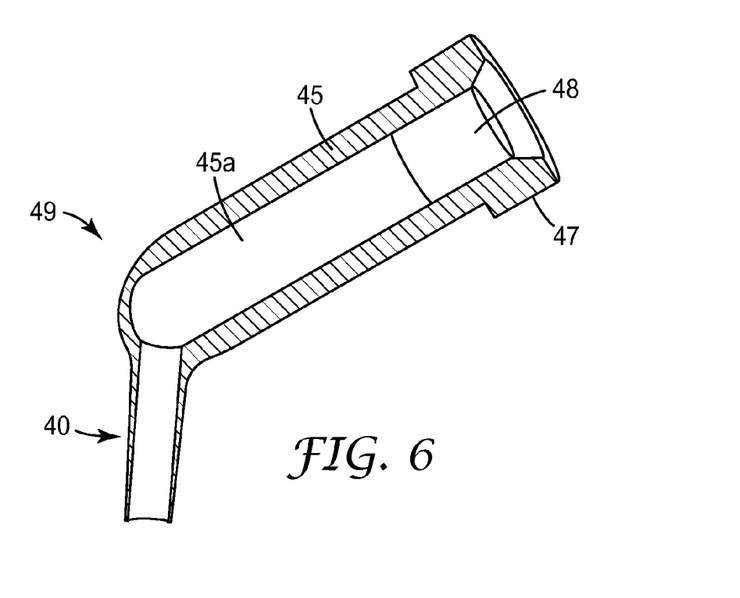
FIG. 6 is a cross-sectional view of a system for dispensing a dental material according to another embodiment of the invention.

FIG. 6 shows a system 49 for dispensing a dental material. The system 49 has a cartridge 45 and an application tip 40. In the example the cartridge 45 and the application tip 40 are made in one piece. The cartridge 45 and the tip 40 may for example be monolithically formed of the same material, or formed by two-shot injection molding from two different materials. The cartridge 45 forms a chamber 45a for holding dental material. Further a piston 48 for extruding the dental material is movably and sealingly arranged within the chamber 45a. The cartridge 45 in the example has a coupling 47 which can be retained in a dispensing gun (not shown) for dispensing the dental material.

Figure 7:
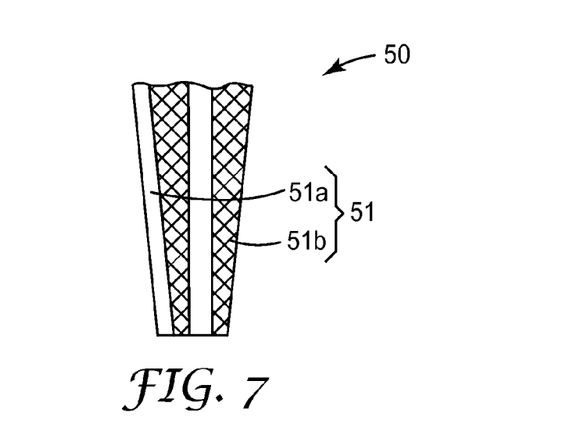
FIG. 7 is a cross-sectional view of an application tip according to a still a further embodiment of the invention including FIGS. 7a,7b illustrating details of the application tip shown.

FIG. 7 shows an application tip 50 having a dispensing end 51. The dispensing end 51 comprises first wall portions 51a and second wall portions 51b. The first wall portions 51a and the second wall portions 51b are arranged in a circumferentially alternating manner. The first wall portions 51a are made of a first plastic material and the second wall portions 51b are made of a different second plastic material. The first plastic material is preferably less resilient than the second plastic material. Further the first plastic material may be selected from among polyethylene (PE), polypropylene (PP), polyoxymethylene (POM), polybutadiene terephthalate (PBT), acrylonitrile-butadiene-styrene terpolymer (ABS), and polyamide (PA). The second plastic plastic material may be selected from among a thermoplastic elastomer, silicone or rubber material.

Figure 7A:
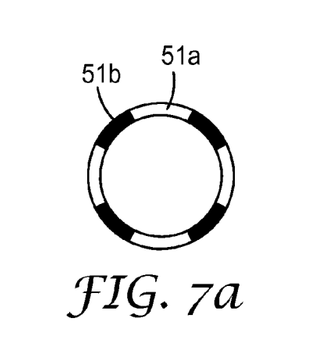
Figure 7B:
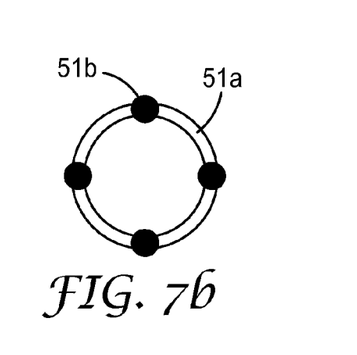

FIG. 7a is a front view on the dispensing end 51 at an initial stage. At the stage shown in FIG. 7b the second wall portions 51b are compressed, for example in response of radial forces on the outside of the dispensing end 51. Thus the dispensing end may be adapted to penetrate in narrow cavities, for example a cavity in a tooth.

The invention claimed is:

1. A system for dispensing a dental material, comprising:
a cartridge with a chamber for holding the dental material; and
an application tip adapted for removably coupling with a dispensing nozzle of the cartridge and dispensing the dental material in the chamber, wherein the application tip comprises a tubular dispensing end having an outer conical surface with a first diameter $D_{o1}$ and a second diameter $D_{o2}$, with $D_{o2}$ greater than $D_{o1}$, and an inner conical surface with a first diameter $D_{i1}$ and a second diameter $D_{i2}$, with $D_{i2}$ greater than $D_{i1}$, wherein the inner conical surface forms a conduit through the application tip to form a dispensing opening, the dispensing end being formed of a circumferential wall having a thickness $T_1$ and which forms the dispensing opening of a diameter $D_{i1}$, the dispensing end having a diameter-to-thickness-ratio $D_{i1}:T_1$ at the dispensing opening which is at least 13 or greater, wherein the wall thickness of the application tip increases in a direction away from the opening and wherein the wall and comprises:
a first wall portion of a first plastic material selected among polyethylene (PE), polypropylene (PP), polyoxymethylene (POM), polybutadiene terephthalate (PBT), acrylonitrile-butadiene-styrene terpolymer (ABS), and polyamide (PA), and
a second wall portion formed of a second plastic material selected from among a thermoplastic elastomer, silicone or rubber, wherein the first plastic material is less resilient than the second plastic material, and
wherein the second wall portion is arranged adjacent the dispensing opening and the first wall portion is arranged further away from the dispensing opening.

2. The system of claim 1, wherein the application tip and the cartridge are formed in one piece.

3. The system of claim 1, wherein the application tip and the cartridge are formed in at least two separate pieces and being adapted for connecting with each other.

4. The system of claim 1, comprising a dental restorative material selected from among a composite, a bis-acrylic composite, and a glass ionomer.

5. The system of claim 1, wherein the inner conical surface forms a conduit through the application tip to form a first dispensing opening with a circular cross section and a first open area, and wherein the second plastic material is sufficiently resilient such that the dispensing end, when laterally deformed, forms a second dispensing opening with oval cross section and a second open area less than the first open area.

6. The system of claim 1, wherein the diameter $D_{i1}$ is within a range of 1 mm to 2.5 mm and the thickness $T_1$ is within a range of 0.05 mm and 0.19 mm.

7. The system of claim 1, having a predetermined breaking linkage in the transition between the first and second wall portions.

8. The system of claim 1, wherein the first and second wall portion are linked by a positive fit or friction fit.

9. The system of claim 1, wherein the wall has at least one slit extending from the opening in a direction away from the opening.

10. The system of claim 1, further comprising a piston which is movably arranged within the chamber for extruding the dental material.

11. The system of claim 10, further comprising a dispensing gun for removably receiving the cartridge and comprising a plunger for urging the piston forward for dispensing the dental material.

12. A system for dispensing a dental material, comprising:
a cartridge with a chamber for holding the dental material; and
an application tip adapted for removably coupling with a dispensing nozzle of the cartridge and dispensing the dental material in the chamber, wherein the application tip comprises a tubular dispensing end having an outer conical surface with a first diameter $D_{o1}$ and a second diameter $D_{o2}$, with $D_{o2}$ greater than $D_{o1}$, and an inner conical surface with a first diameter $D_{i1}$ and a second diameter $D_{i2}$, with $D_{i2}$ greater than $D_{i1}$, wherein the inner conical surface forms a conduit through the application tip to form a dispensing opening, the dispensing end being formed of a circumferential wall having a thickness $T_1$ and which forms the dispensing opening of a diameter $D_{i1}$, the dispensing end having a diameter-to-thickness-ratio $D_{i1}:T_1$ at the dispensing opening which is at least 13 or greater, wherein the wall thickness of the application tip increases in a direction away from the opening, and wherein the wall comprises:
a first wall portion of a first plastic material chosen from polyethylene (PE), polypropylene (PP), polyoxymethylene (POM), polybutadiene terephthalate (PBT), acrylonitrile-butadiene-styrene terpolymer (ABS), and polyamide (PA), and
a second wall portion formed of a second plastic material chosen from a thermoplastic elastomer, silicone or rubber, wherein the first plastic material is less resilient than the second plastic material, and
wherein the first wall portion and the second wall portion are arranged in a circumferentially alternating manner.

13. The system of claim 12, further comprising a piston which is movably arranged within the chamber for extruding the dental material.

14. The system of claim 13, further comprising a dispensing gun for removably receiving the cartridge and comprising a plunger for urging the piston forward for dispensing the dental material.

* * * * *